(12) United States Patent
Flaherty

(10) Patent No.: US 7,858,037 B2
(45) Date of Patent: Dec. 28, 2010

(54) ADAPTOR FOR SAMPLE VIAL

(75) Inventor: James Edward Flaherty, Attleboro, MA (US)

(73) Assignee: Instrumentation Laboratory Company, Lexington, MA (US)

(*) Notice: Subject to any disclaimer, the term of this patent is extended or adjusted under 35 U.S.C. 154(b) by 317 days.

(21) Appl. No.: 12/077,988

(22) Filed: Mar. 24, 2008

(65) Prior Publication Data

US 2008/0240990 A1  Oct. 2, 2008

Related U.S. Application Data

(60) Provisional application No. 60/920,951, filed on Mar. 30, 2007.

(51) Int. Cl.
    *G01N 33/50* (2006.01)

(52) U.S. Cl. .................. 422/68.1; 422/63; 422/99; 422/100; 604/403

(58) Field of Classification Search ............ 600/577; 422/68, 99, 100
    See application file for complete search history.

(56) References Cited

U.S. PATENT DOCUMENTS

| | | | |
|---|---|---|---|
| 3,931,815 A | 1/1976 | Takatsuki | |
| 4,435,177 A | 3/1984 | Kuhlemann et al. | |
| 4,512,766 A * | 4/1985 | Vailancourt | 604/167.03 |
| 4,559,043 A * | 12/1985 | Whitehouse et al. | 604/201 |
| 4,731,059 A | 3/1988 | Wanderer et al. | |
| 5,049,129 A | 9/1991 | Zdeb et al. | |
| 5,074,839 A | 12/1991 | Choksi et al. | |
| 5,137,511 A | 8/1992 | Reynolds | |
| 5,284,570 A | 2/1994 | Savage et al. | |
| 5,397,303 A | 3/1995 | Sancoff et al. | |
| 5,478,337 A | 12/1995 | Okamoto et al. | |
| 6,036,680 A | 3/2000 | Horne et al. | |
| 6,551,299 B2 | 4/2003 | Miyoshi et al. | |
| 6,637,470 B2 | 10/2003 | Reihl et al. | |
| 7,294,122 B2 | 11/2007 | Kubo et al. | |
| 7,326,194 B2 | 2/2008 | Zinger et al. | |
| 2006/0263250 A1 | 11/2006 | Blouin et al. | |

OTHER PUBLICATIONS

International Search Report for International Application No. PCT/US2008/03839, dated Jun. 20, 2008 (2 pages).
Written Opinion for International Application No. PCT/US2008/003839, mailed Jun. 20, 2008 (4 pages).
Supplementary European Search Report and Annex to the European Search Report, dated, Jun. 22, 2010 from co-pending European Patent Application EP 08 72 7116, Filed on Mar. 28, 2008.

* cited by examiner

*Primary Examiner*—Jill Warden
*Assistant Examiner*—Sharon Pregler
(74) *Attorney, Agent, or Firm*—Burns & Levinson, LLP; Ronda P. Moore, D.V.M.

(57) ABSTRACT

The invention relates generally to a sample vial adaptor for interfacing a sample vial with the sample port of a diagnostic instrument, in particular a sample vial containing a patient body fluid sample with the sample port and sample pathway of a multi-use diagnostic instrument. Embodiments of the sample vial adaptor according to the invention generally include a short exterior vent tube having one end in communication with a chamber having a vent, an interior collection tube that is longer than the short exterior vent tube, axially positioned in the lumen of the short exterior vent tube and extending to a capillary outlet that is located on the portion of the inner collection tube that is outside of the short exterior vent tube and outside the vented chamber.

14 Claims, 11 Drawing Sheets

ADAPTOR FOR SAMPLE VIAL

This application claims priority to and benefit of U.S. provisional application 60/920,951, filed Mar. 30, 2007 incorporated by reference herein in its entirety.

TECHNICAL FIELD

The invention relates generally to adaptors for transfer of fluids from a container to an instrument, and methods thereof. More particularly, the invention relates to a sample vial adaptor for interfacing a sample vial with the sample port of a diagnostic instrument, in particular a sample vial containing a patient body fluid sample with the sample port and sample pathway of a multi-use diagnostic instrument.

BACKGROUND

On an annual basis, tens of millions of people have their blood drawn and tested to provide immediate physiological diagnostics necessary for caregivers to quickly administer the appropriate treatment to the patient. For example, recently, a growing market segment in the area of "near patient" critical care testing specifically addresses enhanced renal function testing. Renal function testing uses a panel of analytes including Na, iCa, Cl, K, $HCO_3$, glucose, lactate, blood urea nitrogen (BUN) and creatinine. The renal panel incorporates three measurements also included in a typical electrolyte/metabolite panel, i.e., creatinine, BUN and measured $HCO_3$.

Acute renal failure (ARF) is defined as an abrupt or rapid decline in renal function. A rise in BUN or creatinine concentrations is usually evidence of ARF. ARF is often transient and completely reversible. $HCO_3$ is a critical parameter in assessing acid-base balance as it relates to renal function. While carbon dioxide ($CO_2$) is the respiratory component in acid-base balance, bicarbonate ($HCO_3$) is the renal component. A blood sample vial, e.g., a Vacutainer® (BD) vial, is used for collecting blood samples from patients.

Often when testing is performed at an outside laboratory, a blood sample is drawn into a heparinized vial, e.g., a Vacutainer® vial, aliquoted into syringe(s), and capped prior to transport or upon receipt in the laboratory. In the operating or emergency room, the sample is prepared in either syringes or poured into smaller cuvettes to accommodate the short sampling probe lengths typical of diagnostic instruments. The short probe length prohibits direct sampling by the diagnostic instrument from an open Vacutainer® vessel. Most multi-use, high volume diagnostic instruments have sample ports that are primarily designed to interface with syringes.

A common sampling error occurs when a diagnostic instrument aspirates a sample from a capped airtight sample vial. As a volume of sample is withdrawn from the sample vial by the diagnostic instrument, a vacuum is introduced in the vial. When the vial is removed from the sample port of the diagnostic instrument, the pressure in the sample pathway of the instrument equilibrates with the atmosphere causing air to rush into the sample pathway and the sample to be pulled further into the sample pathway past the sample sensor area. A sampling error is triggered and the sample is not measured.

SUMMARY OF THE INVENTION

In order to avoid the aliquotting step necessary in current devices and methods, and to allow an immediate, direct access to the sample vial through the vial cap obviating the need to uncap the sample vial and expose the handler to biohazardous material, a specific sample vial adaptor that interfaces the capped vial with the sample port of a diagnostic instrument is needed.

The sample vial adaptor described herein resolves the sampling error, reduces sample cross-contamination, operator biohazard exposure, and the large sample size needed for current devices and methods for introducing a sample into a diagnostic instrument. Additionally, one end of the sample vial adaptor described herein according to the invention interfaces with a diagnostic instrument sample port in a manner consistent with a capillary sample device.

In one aspect, the invention relates to a device for removal of a body fluid from a vial, comprising an elongate body sub-assembly including a first portion, a second portion, and an intermediate portion extending from the first portion to the second portion. The first portion of the elongate body sub-assembly includes a first cylindrical chamber having a wall surrounding a lumen and at least one hole extending from the lumen through the wall to the exterior of the elongate body. The intermediate portion of the elongate body sub-assembly comprises a channel extending from the first cylindrical chamber to the second portion of the elongate body sub-assembly. The second portion of the elongate body sub-assembly includes a second chamber narrower than the first chamber. The second chamber includes a wall surrounding a lumen. The lumen is in fluid communication with the exterior of the elongate body sub-assembly.

A threaded sub-assembly of the device comprises a first end having a threaded exterior surface, and a second end positioned within the lumen of the first chamber of said elongate body sub-assembly.

The device according to the invention further includes a vent tube comprising a lumen, a first end, and a second end. The vent tube is axially positioned and fixed in the threaded sub-assembly. The second end of the vent tube is in fluid communication with the lumen of the first chamber. The first end of the vent tube comprises a bevel and extends beyond the first end of the threaded sub-assembly.

The device further includes a collection tube comprising a lumen, a first end, and a second end. The collection tube is axially disposed in the lumen of the vent tube. The second end of the collection tube is in fluid communication with the second chamber of the elongate body sub-assembly and the first end of the collection tube extends beyond the first end of the first tube. A gap is disposed between the vent tube and the collection tube. The gap is uniform in width and extends along the length of the vent tube.

In another aspect, the invention recites a method using the sample vial adaptor described herein for introducing a fluid sample from a sample vial into the sample port of a diagnostic instrument.

BRIEF DESCRIPTION OF THE FIGURES

In the drawings, like reference characters generally refer to the same parts throughout the different views. The drawings are not necessarily to scale, emphasis instead generally being placed upon illustration of the invention.

DESCRIPTION OF THE INVENTION

In general, in one aspect, the invention relates to a sample vial adaptor for interfacing a sample vial, for example, a sample vial containing a body fluid from a patient, with a sample port of a multi-use, typically high volume diagnostic instrument such as the GEM 4000 marketed by Instrumentation Laboratory Company (Lexington, Mass.), and methods of use thereof.

All of the following embodiments of the sample vial adaptor according to the invention generally have common features including a short exterior vent tube having one end in communication with a chamber having a vent, an interior collection tube that is longer than the short exterior vent tube, axially positioned in the lumen of the short exterior vent tube and extending to a capillary outlet that is located on the portion of the inner collection tube that is outside of the short exterior vent tube and outside the vented chamber.

The sample vial adaptor according to the invention is advantageous over prior art devices because air flows back into the sample vial, away from the sample input through the vent thereby equilibrating the vial to room atmospheric conditions. This equilibration allows an unrestricted flow of sample from the vial into a sample port in the diagnostic instrument and consequently proper sample positioning in the instrument. Without a "breathing" vent, residual vacuum will build up in the closed sample vial during sample aspiration, and upon removal of the sample container, the equalization of the sample path to atmospheric pressure causes the sample to be pulled past the sensor area, triggering a sample detection flag and reported system error.

Moreover, the sample vial adaptor according to the invention utilizes a collection tube and vent tube arranged concentrically which minimizes the outer dimension of the combined tubes and permits accurate targeting to and penetration of the center of the vial cap where puncturing is most desirable. The concentric arrangement of the tubes enhances their rigidity and aids in penetration of the tubes through the cap. The concentric arrangement also aids in manufacturing and ease of assembly of the adaptor.

Figure 1:
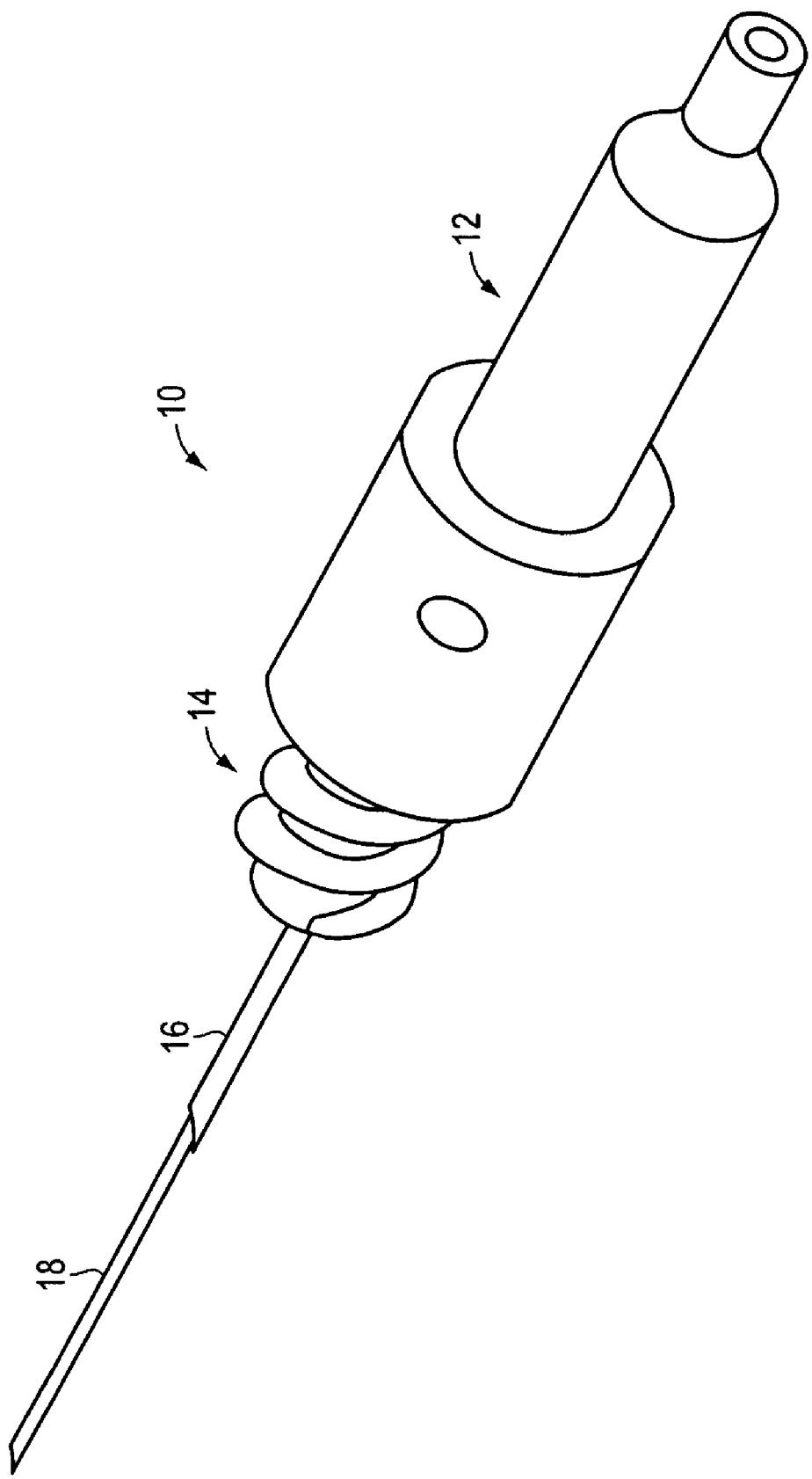
FIG. 1 is a perspective view of a sample vial adaptor according to an illustrative embodiment of the invention.

Referring to FIG. 1, the sample vial adaptor 10 according to one embodiment of the invention includes an elongate body sub-assembly 12, a threaded sub-assembly 14, a vent tube 16, and a collection tube 18.

Figure 2:
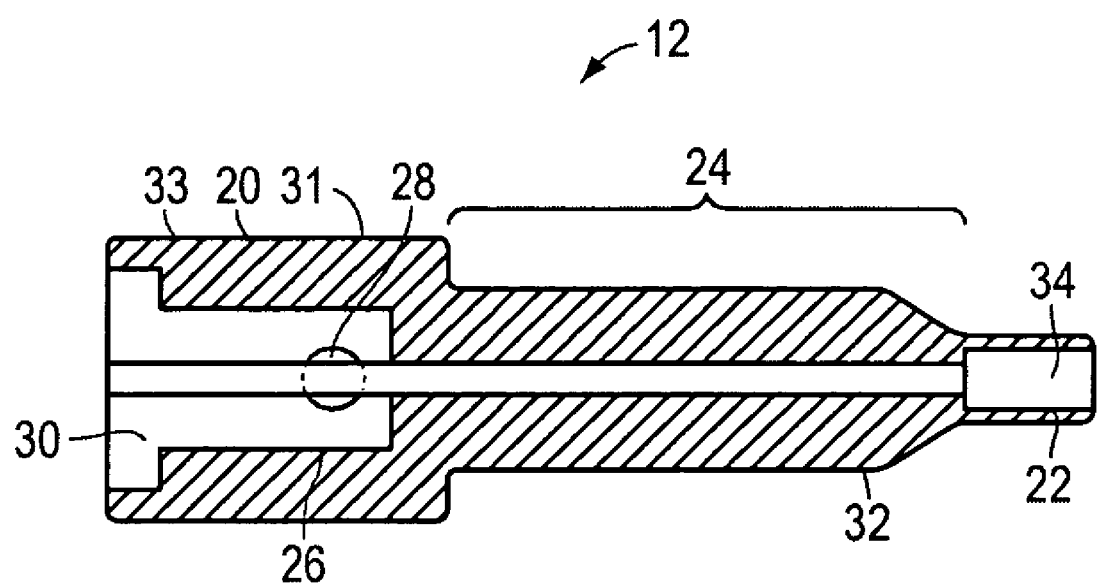
FIG. 2 is a cross-sectional view of the elongate body sub-assembly of the sample vial adaptor according to an illustrative embodiment of the invention.

Referring to FIG. 2, in one embodiment of the invention, the exemplary elongate body sub-assembly 12 has a first portion 20, a second portion 22, and an intermediate portion 24 extending from the first portion 20 to the second portion 22. The first portion 20 of the elongate body sub-assembly 12 includes a first chamber 26, for example, a cylindrical chamber. The first chamber 26 includes a vent 28 such as a hole that extends from the lumen 30 of the first chamber 26 through the wall 33 of the elongate body sub-assembly 12 to the surface 31 of the elongate body sub-assembly 12. The vent 28 allows communication of atmospheric air from outside the first chamber 26 with the first chamber lumen 30.

The first chamber 26 also serves as a receptacle for the threaded subassembly described below.

With continued reference to FIG. 2, the exemplary vent 28 may be positioned anywhere on the first chamber wall 33. In a particular embodiment of the invention, the first chamber 26 may have more than one vent 28 such as two, three, four or more vents. The shape of the vent 28 may be, for example, cylindrical, rectangular, or funnel shaped, to name a few shapes. Other vent shapes are also contemplated and the vent shape is not limited to the shapes disclosed.

Further features of the elongate body sub-assembly 12 include a channel 32 longitudinally disposed in the intermediate portion 24. Referring to the illustrative embodiment shown in FIG. 2, the channel 32 extends from the first chamber 26 to the second portion 22 of the elongate body sub-assembly 12. The channel 32 is in fluid communication with the lumen 30 of the first chamber 26. Channel 32 may also receive a portion of the collection tube 18.

An additional feature of the elongate body sub-assembly 12 includes a second chamber 34, illustrated in FIG. 2, positioned at the end of the channel 32 opposite to the end of the channel 32 that is in fluid communication with the first chamber 26. The second chamber 34 is positioned in the second portion 22 of the elongate body sub-assembly 12 and is in fluid communication with the channel 32.

Figure 3:
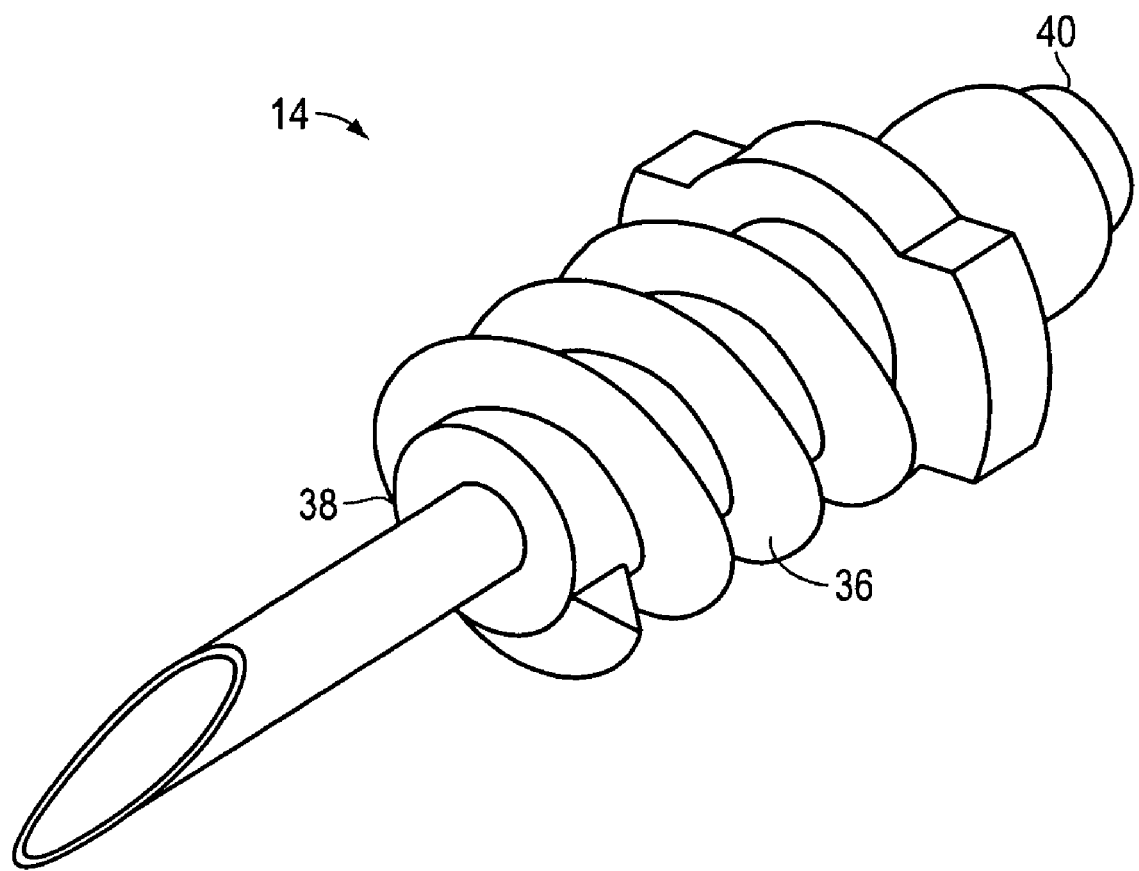
FIG. 3 is a perspective view of the threaded sub-assembly of the sample vial adaptor according to an illustrative embodiment of the invention.

FIG. 3 is a perspective view of an illustrative embodiment of the threaded sub-assembly according to the invention. In one embodiment of the invention, the threaded sub-assembly 14 includes a threaded member 36, a first end 38, and a second end 40. In one embodiment, the threaded member 36 includes threads spiraling outwardly from the external surface of the threaded member 36. The threads begin at the first end 38 and extend towards but not to the second end 40. The spiral may be right handed or left handed. The second end 40 of the threaded member 36 does not include threads and is generally shaped to be received in the first chamber 26 at the first end 20 of the elongate body sub-assembly 12. In one embodiment, the threads may interlock with a receptacle, for example, a cylindrical holder discussed below with respect to FIG. 7, having corresponding interlocking threads.

The threaded sub-assembly may include other external interlocking devices such as a snap-lock or other devices in addition to or in place of the threads for interlocking with a corresponding interlocking piece.

Figure 4A:
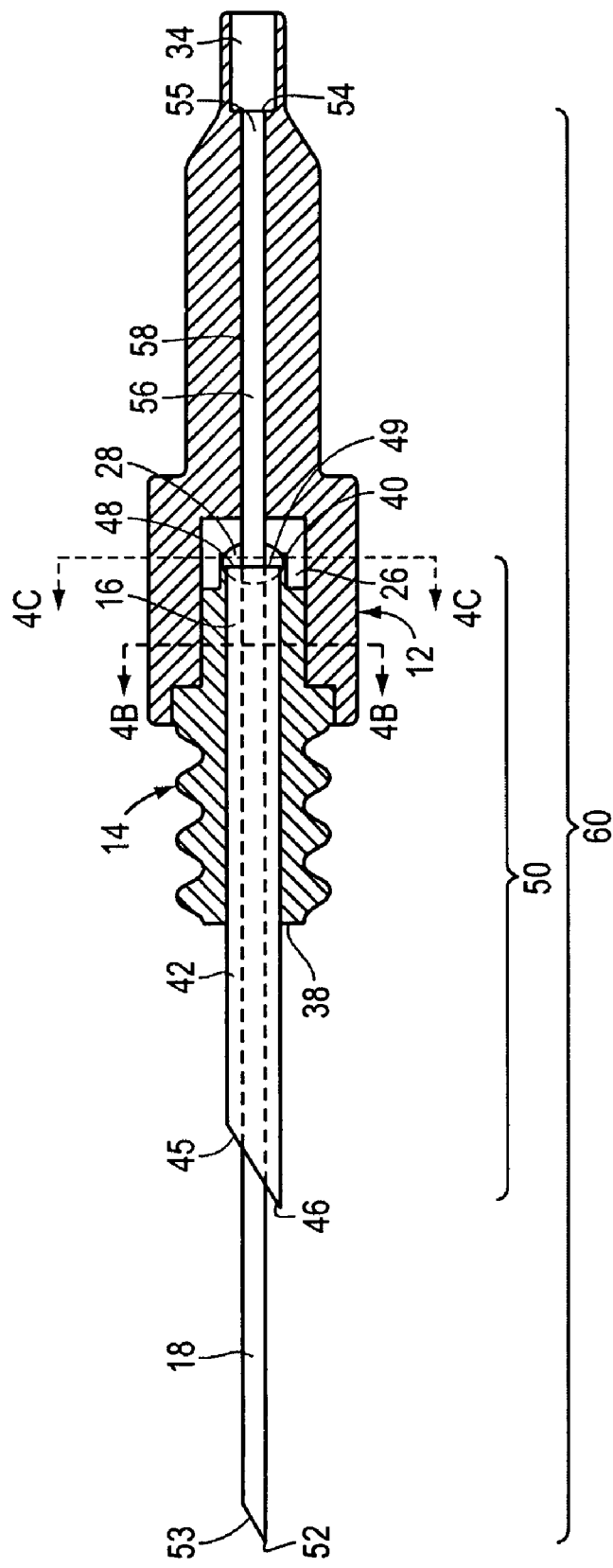
FIG. 4A is a longitudinal cross-sectional view of the sample adaptor including the vent tube and the collection tube according to one embodiment of the invention.
Figure 4B:
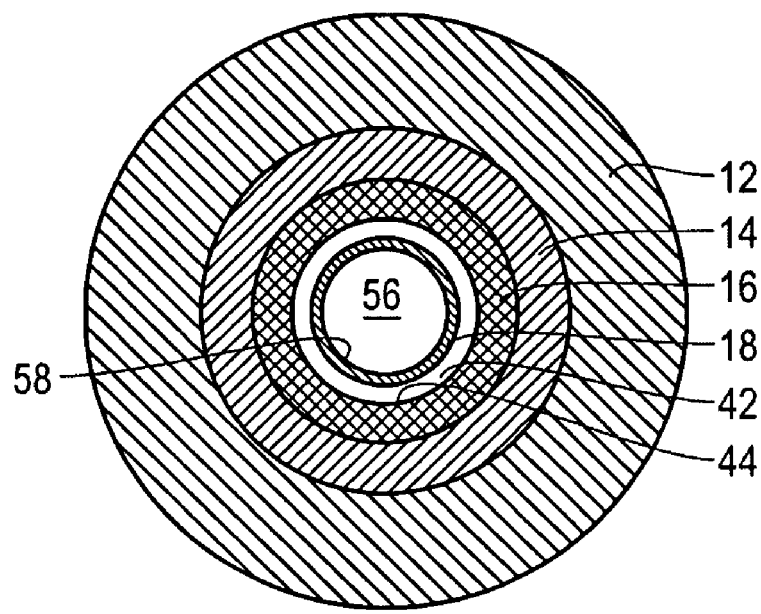
FIG. 4B is a transverse cross-sectional view taken at 4b-4b of FIG. 4A.
Figure 4C:
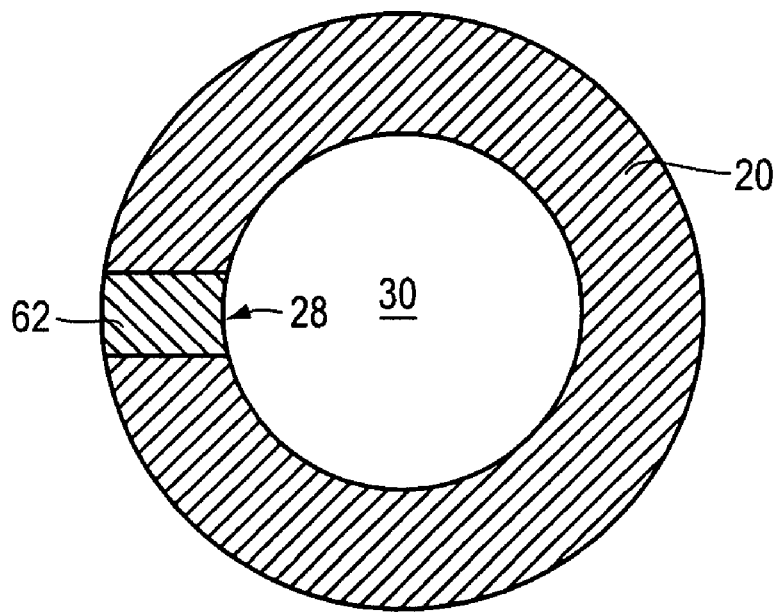
FIG. 4C is a transverse cross-sectional view of the first portion of the elongate body subassembly, the first chamber lumen, and the vent taken at 4c-4c of FIG. 4A.

FIG. 4A is a longitudinal cross-sectional view, FIGS. 4B and 4C are transverse cross-sectional views of an illustrative embodiment of the sample vial adaptor. Referring to FIGS. 4A-4C, the exemplary vent tube 16 is axially disposed in the threaded sub-assembly 14. The vent tube 16 has a first end 46, a second end 48, a lumen 42, a wall 44 and a length 50. The first end 46 typically includes a beveled opening 45 in communication with the vent tube lumen 42 and ends in a point, i.e., a tip having an acute angle. The first end 46 is positioned at a fixed distance outside of the first end 38 of the threaded sub-assembly 14. The second end 48 of the vent tube 16 includes an opening 49 to the lumen 42 and is positioned near the second end 40 of the threaded sub-assembly 14. The opening 49 of the second end 48 of the vent tube 16 is positioned near the vent 28 in fluid communication with the first chamber 26 of the elongate member sub-assembly 12.

With continued reference to FIGS. 4A-4C, the collection tube 18 is axially disposed in the lumen 42 of the vent tube 16. A gap separates the exterior of the collection tube 18 from the wall of the vent tube 16. Typically, the gap is uniform along the length of the vent tube 16. The collection tube 18 has a first end 52, a second end 54, a lumen 56, a wall 58, and a length 60. The first end 52 typically includes a beveled opening 53 in communication with the lumen 56 and terminates with a point, i.e., a tip having an acute angle. The first end 52 of the collection tube 18 is positioned outside of the lumen 42 of the vent tube 16 at a fixed distance beyond the first end 46 of the vent tube 16. The second end 54 of the collection tube 18 is positioned at a fixed distance from the second end 48 of the vent tube 16 within the channel 32 (see FIG. 2) of the elongate body sub-assembly 12. The second end 54 includes an opening 55 in fluid communication with the lumen 56 and is positioned adjacent to and in fluid communication with the second chamber 34.

Figure 5:
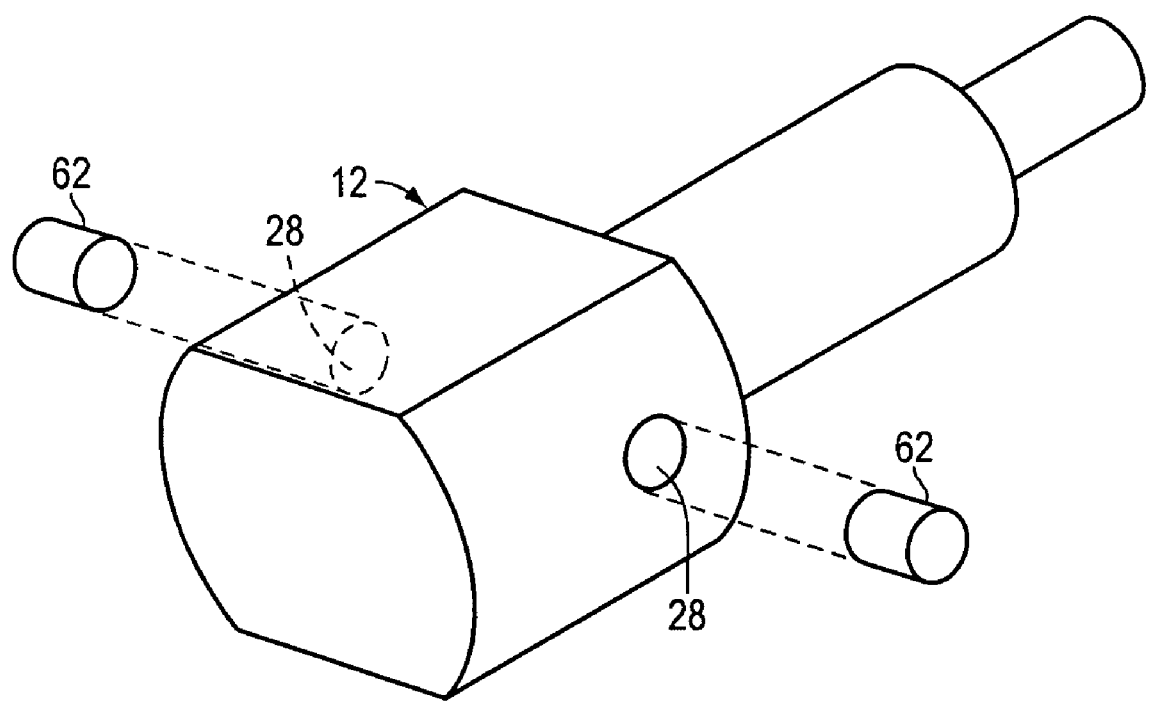
FIG. 5 is a perspective view of the elongate body subassembly of the sample vial adaptor including one or more vents and vent plugs according to an illustrative embodiment of the invention.

Referring to FIG. 5, the one or more vents 28 may house a porous material, for example, a porous plug 62 made from, for example a porated polymer. Features of the porous material permit the transfer of air but not fluid through the vent 28.

Referring to FIGS. 6A-6D, in another aspect, the invention recites a method using the sample vial adaptor described herein for introducing a fluid sample from a sample vial into the sample port of a multi-use diagnostic instrument, for example, the GEM 4000 diagnostic instrument manufactured and sold by Instrumentation Laboratory Company (Lexington, Mass.).

Figure 6A:
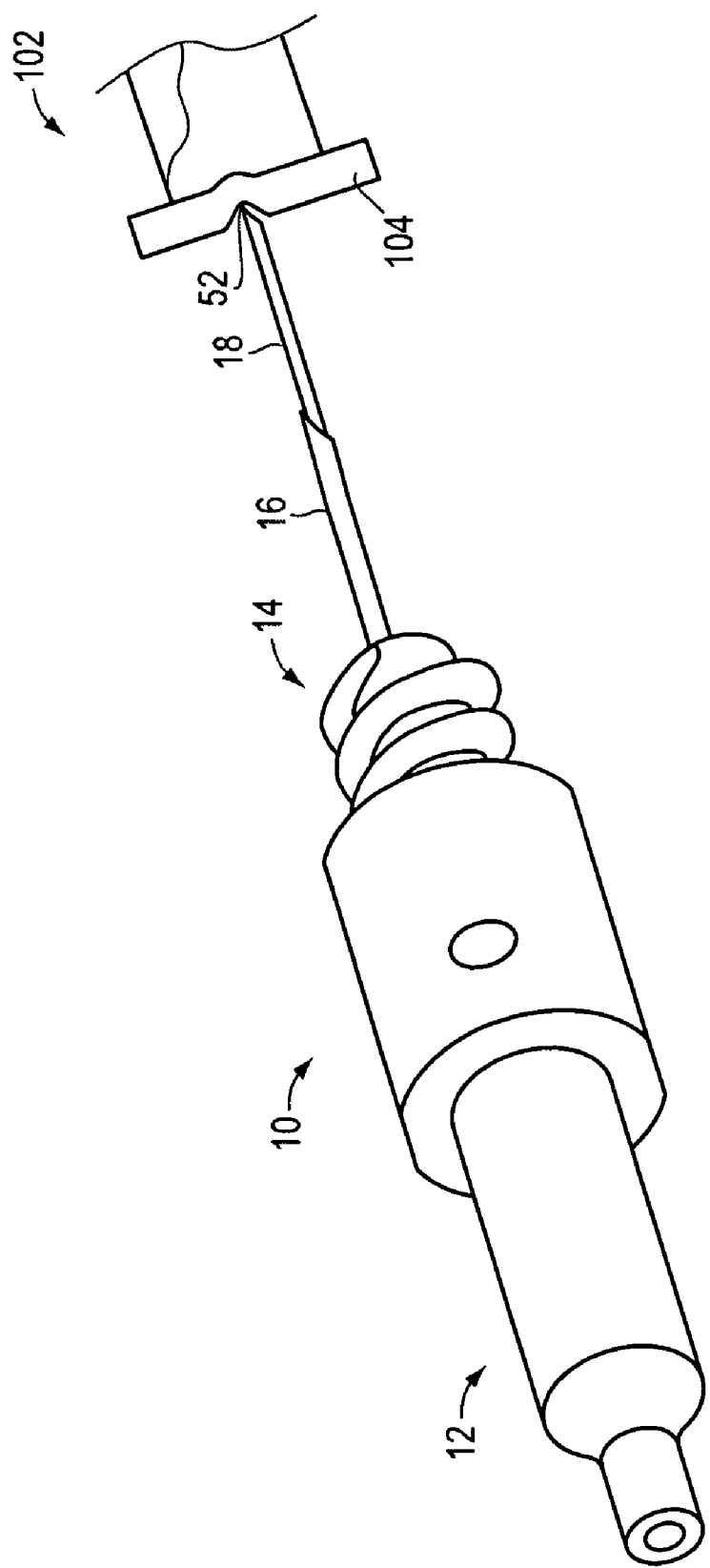
FIGS. 6A-6D illustrate an exemplary method for introducing a sample from a sample vial into the sample port of a diagnostic instrument using the exemplary sample vial adaptor according to the invention.

FIG. 6A illustrates an exemplary sample vial adaptor 10 and a sample vial 102 including an airtight cap 104. The pointed end 52 of the collection tube 18 is inserted into the cap 104, such as a rubber, plastic, or other stopper, of the vial 102.

Figure 6B:
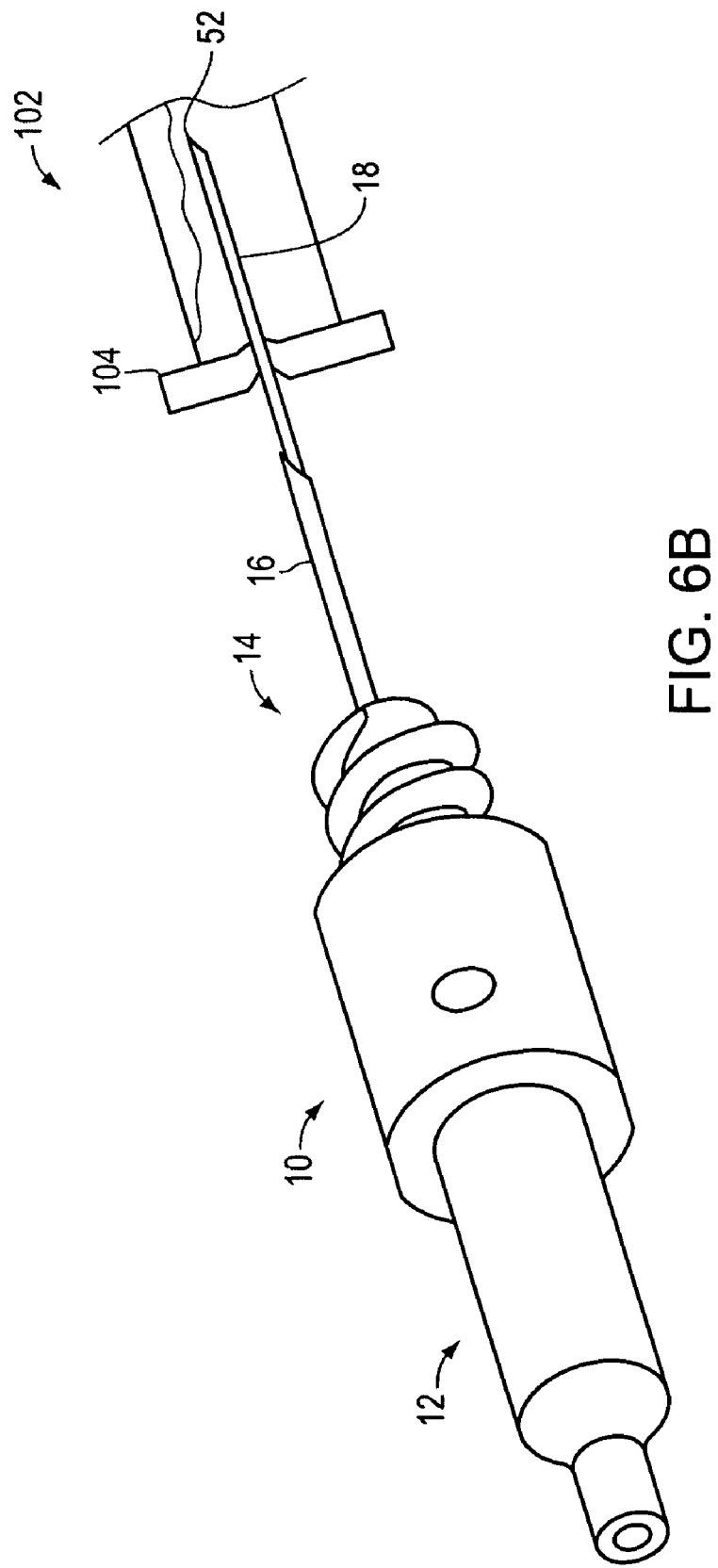

FIG. 6B illustrates the sample vial adaptor 10 shown in FIG. 6A as the sample tube 18 of the sample vial adaptor 10 is pushed further into the vial 102 through the cap 104.

Figure 6C:
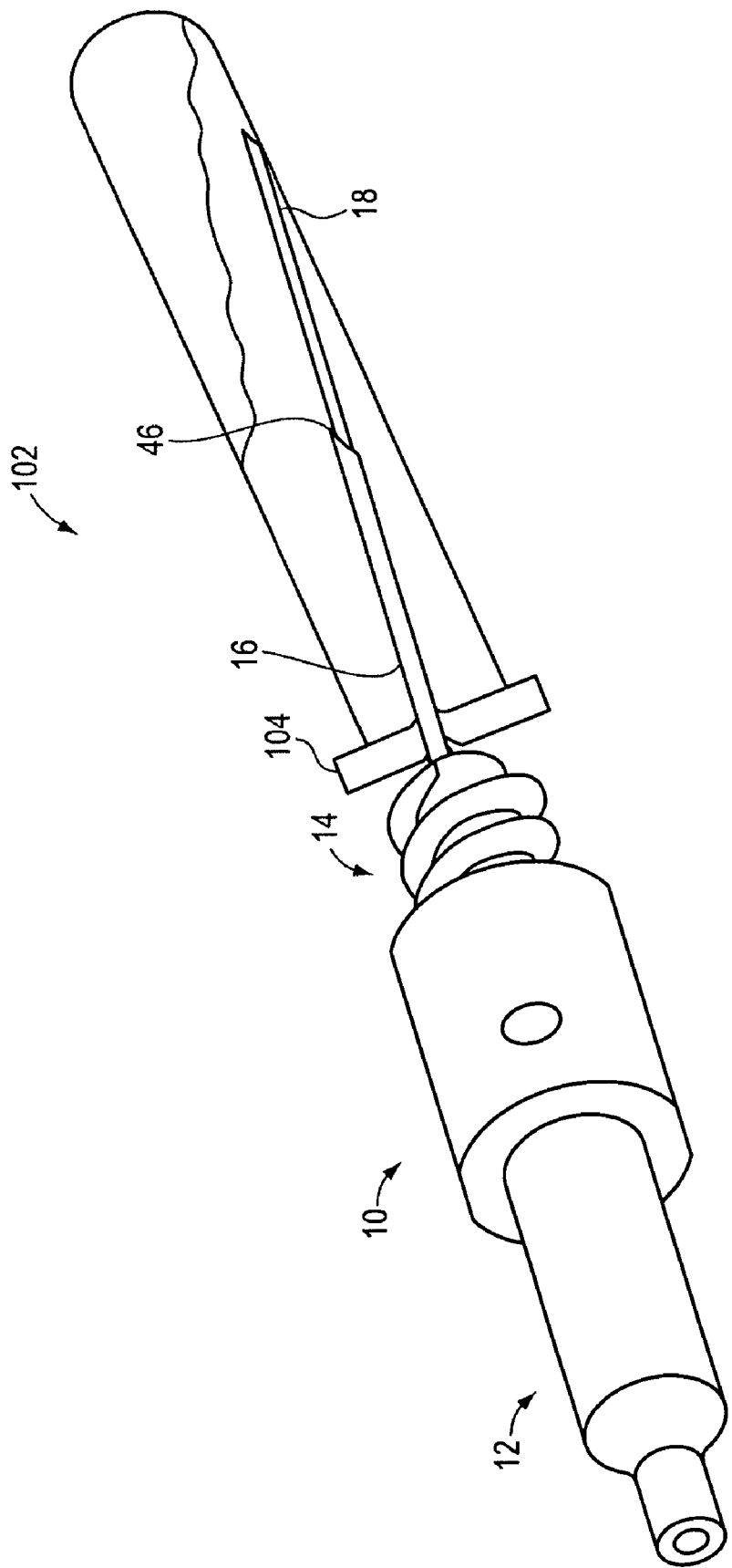

FIG. 6C illustrates the sample vial adaptor shown in FIG. 6B with the pointed first end 46 of the vent tube 16 pushed through the cap 104 into the vial 102. The tip of the first end 46 of the vent tube 16 is positioned between the cap 104 and the sample fluid.

Figure 6D:
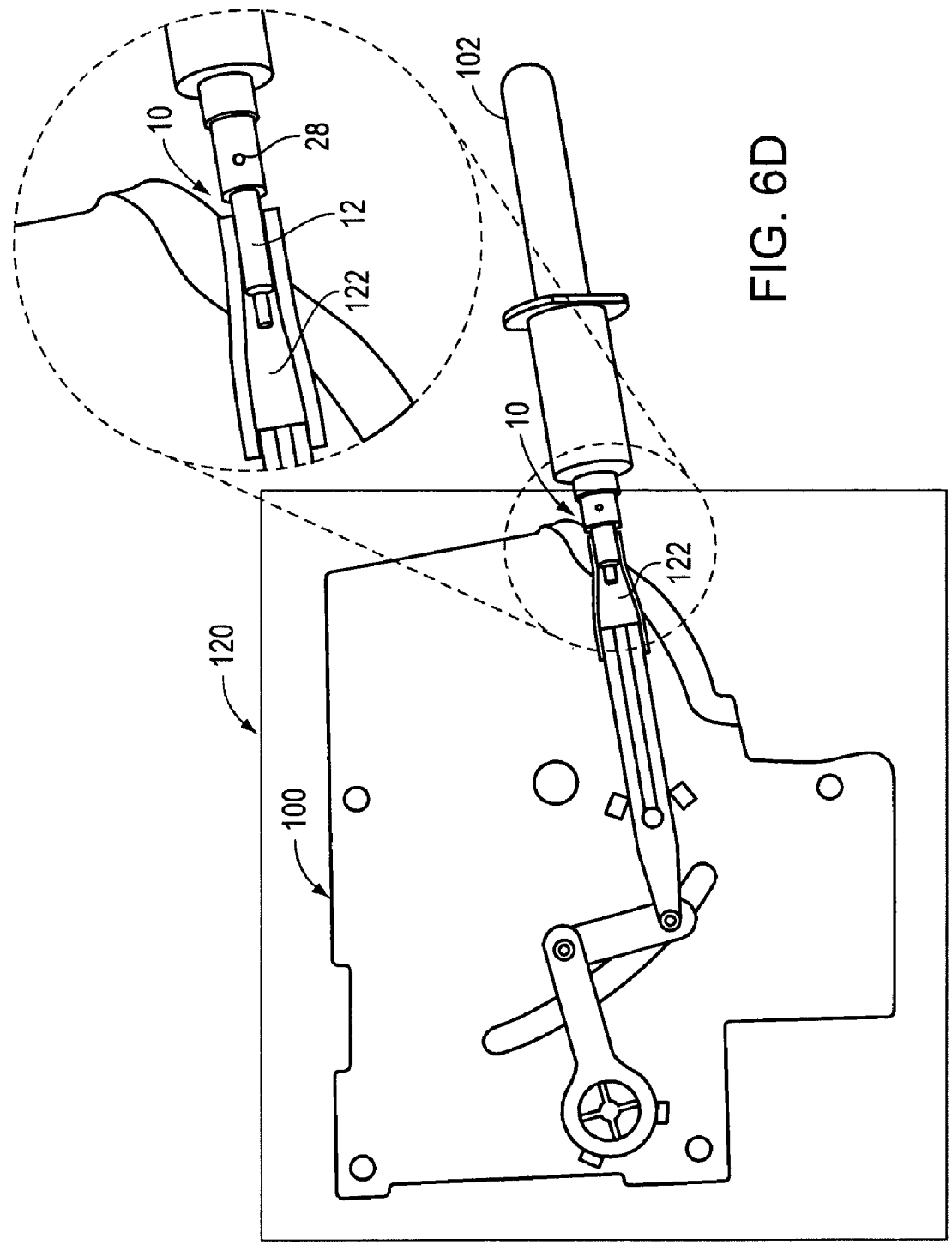

FIG. 6D illustrates an exemplary aspirator assembly 100 of a multi-use diagnostic instrument 120, and a sample vial 102 joined with an exemplary sample vial adaptor 10, as shown in FIG. 6C. The sample vial adaptor 10 in combination with the sample vial 102 is introduced into a sample port 122 of the aspirator assembly 100 of the multi-use diagnostic instrument 120. In one embodiment of the method, the elongate body sub-assembly 12 is inserted into the sample port 122. Alternatively, the sample port 122 is inserted into the second chamber of the elongate body sub-assembly 12. The sample fluid is aspirated from the vial 102, through the lumen of the collection tube, and into the sample port 122. Simultaneous with aspiration of the sample fluid, as fluid is displaced from the vial, air is drawn in through the vent 28 of the sample vial adaptor 10, into the second end of the vent tube and exits through the first end of the vent tube into the sample vial 102. The volume of air taken into the vial via the vent replaces the volume of liquid that is aspirated and eliminates the build up of an undesirable vacuum in the vial.

Figure 7:
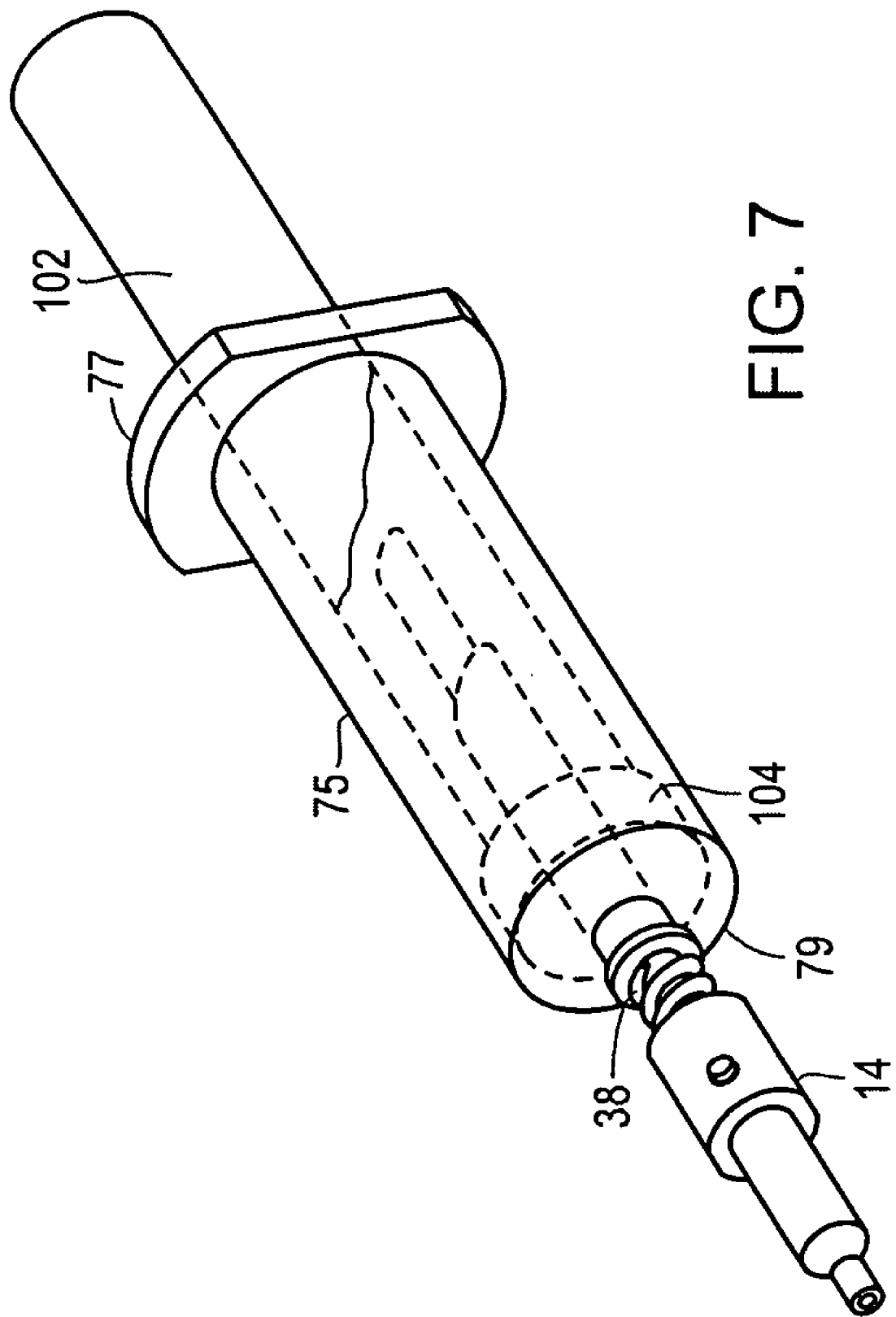
FIG. 7 is a perspective view of the sample vial adaptor including a vial holder according to an illustrative embodiment of the invention.

FIG. 7 illustrates a vial holder for aiding in alignment of a sample vial 102 and vial cap 104 for puncturing the vial cap 104 by the end 52 of the collection tube 18 and the end 46 of the vent tube 16. The holder 75 features a cylinder open at a first end 77 and reversibly connected at a second end 79 to the first end 38 of the threaded member 14. The holder 75 may feature threads at the second end 79 that reversibly interface and mate with the first end of the threaded member 14. In a particular embodiment, the holder 75, such as a cylinder, encloses the vent tube 14 and the collection tube 18.

While this invention has been described with reference to illustrative embodiments, this description is not intended to be construed in a limiting sense. Various modifications of the illustrative embodiments, as well as other embodiments of the invention, will be apparent to persons skilled in the art upon reference to this description.

What is claimed is:

1. A device for sampling a body fluid in a vial, comprising:
an elongate body sub-assembly comprising a first cylindrical chamber including a wall surrounding a first lumen and at least one hole extending from the first lumen through the wall to the exterior of the elongate body subassembly extending to the atmosphere;
a vent tube comprising a second lumen, a first end, and a second end, the second end of said vent tube in fluid communication with the first lumen of said first cylindrical chamber;
a collection tube comprising a third lumen, a first end, and a second end, said collection tube substantially parallel to and axially disposed in the second lumen of said vent tube, said first end of said collection tube extending beyond said first end of said vent tube and said second end of said collection tube in fluid communication with the exterior of the device.

2. The device of claim 1 wherein said sub-assembly comprises a first portion, a second portion, and an intermediate portion extending between the first portion and the second portion, said first cylindrical chamber located in the first portion of the subassembly.

3. The device of claim 2 wherein said intermediate portion comprises a channel extending from the first cylindrical chamber to the second portion.

4. The device of claim 3 wherein said second portion comprises a second chamber comprising a fourth lumen.

5. The device of claim 4 wherein said second chamber is in fluid communication with said collection tube and the exterior of the subassembly.

6. The device of claim 1 further comprising a second threaded sub-assembly comprising a first end and a second end, the second end within the first lumen of the first cylindrical chamber.

7. The device of claim 6 wherein said vent tube is axially positioned in the second threaded sub-assembly.

8. The device of claim 1 wherein said first end of said vent tube comprises a bevel and a tip with a point.

9. The device of claim 7 wherein said first end of said vent tube extends outside of said second threaded sub-assembly.

10. The device of claim 1 further comprising a gap between the outside of the collection tube and the wall of the vent tube.

11. The device of claim 1 further comprising a cylinder enclosing said vent tube and said collection tube.

12. The device of claim 3 wherein said third lumen of said collection tube is in fluid communication with said channel, said second chamber and the exterior of said device.

13. The device of claim 1 wherein said second lumen of said vent tube is in fluid communication with said first lumen of said first cylindrical chamber and said hole extending from the first lumen of the first cylindrical chamber to the exterior of said device.

14. A device for removal of a body fluid from a vial, comprising:

an elongate body sub-assembly comprising a first portion, a second portion, and an intermediate portion extending from the first portion to the second portion, said first portion including a first cylindrical chamber including a wall surrounding a first lumen and at least one hole extending from the first lumen through the wall to the exterior of the elongate body, said intermediate portion comprising a channel extending from said first chamber to the second portion of the elongate body sub-assembly, said second portion of said elongate body sub-assembly including a second chamber narrower than the first chamber, said second chamber including a wall surrounding a fourth lumen, said fourth lumen in fluid communication with the exterior of the elongate body sub-assembly extending to the atmosphere;

a threaded sub-assembly comprising a first end comprising a threaded exterior surface, and a second end positioned within the first lumen of the first chamber of said elongate body sub-assembly;

a vent tube comprising a second lumen, a first end, and a second end, said vent tube axially positioned and fixed in the threaded sub-assembly, the second end of said vent tube in fluid communication with the first lumen of said first chamber, said first end of said vent tube comprising a bevel and extending beyond said first end of said threaded sub-assembly;

a collection tube comprising a third lumen, a first end, and a second end, said collection tube axially disposed in the second lumen of said vent tube, said second end of said collection tube in fluid communication with said second chamber of said elongate body sub-assembly and said first end of said collection tube extending beyond said first end of said vent tube; and a gap disposed between said vent tube and said collection tube wherein said gap is uniform in width and extends along the length of the vent tube.

* * * * *